United States Patent [19]

Smith

[11] 4,136,697

[45] * Jan. 30, 1979

[54] FIBERS OF HIGH FLUID-HOLDING CAPACITY

[75] Inventor: Frederick R. Smith, Wilmington, Del.

[73] Assignee: Avtex Fibers Inc., Valley Forge, Pa.

[ * ] Notice: The portion of the term of this patent subsequent to Nov. 11, 1992, has been disclaimed.

[21] Appl. No.: 629,952

[22] Filed: Nov. 7, 1975

Related U.S. Application Data

[60] Division of Ser. No. 625,445, Oct. 24, 1975, Pat. No. 4,041,121, Ser. No. 530,476, Dec. 6, 1974, Pat. No. 3,951,889, and Ser. No. 309,076, Nov. 24, 1972, Pat. No. 3,919,385, said Ser. No. 625,445, is a continuation-in-part of Ser. No. 309,290, Nov. 24, 1972, abandoned, said Ser. No. 530,476, is a division of said Ser. No. 309,076.

[51] Int. Cl.² ..................... A61F 13/20; C08L 1/02; D01F 2/08
[52] U.S. Cl. ..................... 128/285; 260/17.4 CL; 260/17.4 R; 264/191; 264/194
[58] Field of Search ............... 264/185, 184, 191, 194; 260/17.4 R, 17.4 CL; 106/164, 168; 128/284, 285

[56] References Cited

U.S. PATENT DOCUMENTS

| | | | |
|---|---|---|---|
| 2,901,457 | 8/1959 | Stoner et al. | 260/17 R |
| 2,993,018 | 7/1961 | Steinlin | 264/184 |
| 3,377,412 | 4/1968 | Franks | 264/194 |
| 3,521,637 | 7/1970 | Waterbury | 128/285 |
| 3,723,413 | 3/1973 | Chatterjee et al. | 128/285 |
| 3,901,236 | 8/1975 | Assarsson et al. | 128/284 |
| 3,919,385 | 11/1975 | Smith | 264/184 |
| 3,951,889 | 4/1976 | Smith | 128/284 |

Primary Examiner—S. Leon Bashore
Assistant Examiner—Peter Chin
Attorney, Agent, or Firm—Arthur R. Eglington

[57] ABSTRACT

Alloy fibers having high fluid-holding capacity, and a method for making the same, the alloy fibers being comprised of a matrix of regenerated cellulose having polyvinylpyrrolidone dispersed therein. The polyvinylpyrrolidone may be present in combination with an anionic polymer.

19 Claims, No Drawings

FIBERS OF HIGH FLUID-HOLDING CAPACITY

CROSS REFERENCE

This application is a continuation-in-part of my following U.S. patent applications: Ser. Nos. 309,076, filed Nov. 24, 1972 now U.S. Pat. No. 3,919,385; filed Dec. 6, 1974 now U.S. Pat. No. 3,951,889 as a division of my said application 309,076; and 625,445, filed Oct. 24, 1975 now U.S. Pat. No. 4,041,121 as a continuation-in-part of my application 309,290, filed Nov. 24, 1972 abandoned.

The present invention is directed to alloy fibers having high fluid-holding capacity.

Fluid-holding capacity of fibers may be measured by the pellet test described in Example I below or the Syngyna test referred in Example III below. These tests use a pre-determined mass of fibers maintained under external pressure and indicate the amount of water absorbed by the fibers themselves as well as the amount of water retained within the interstices of the mass.

One aspect of this invention relates to absorbent alloy fibers, each having a matrix of regenerated cellulose and polyvinylpyrrolidone uniformly dispersed therein, with the regenerated cellulose being the major portion of the fiber mass. These alloy fibers may be prepared by mixing an aqueous solution of polyvinylpyrrolidone with a filament-forming viscose, shaping the mixture into fibers, coagulating and regenerating the shaped fibers and thereafter drying the same. Viscose constitutes the major portion of the mixture and the shaped alloy fibers are coagulated and regenerated by known means, and preferably in an acid bath containing sulfuric acid and sodium sulfate. The acid bath often contains zinc sulfate as well as other coagulation modifiers as desired.

During the spinning of the viscose into the acid bath, hydrogen ions diffuse into the stream of viscose emerging from each spinneret hole. The reaction of the acid with caustic soda in the viscose produces sodium sulfate and water; the acid also decomposes xanthate groups. The presence of sodium sulfate in the spin bath acts to induce coagulation of the viscose streams owing to dehydration from the interiors of the streams. Zinc ions in the spin bath act, at least at the surfaces of the streams, to convert sodium cellulose xanthate of the viscose to zinc cellulose zanthate which is decomposed more slowly by the acid and thereby keeps the fiber in more stretchable and orientable condition. Typically the temperature of the acid bath is in the range of about 30° to 65° C (such as about 50°-55° C) and the fiber, after passing through the acid bath is subjected to a bath of water (or dilute acid) first at a high temperature such as about 80° C to the boiling point, e.g. about 85°-95° C, and/or to steam, and then to water at a moderate temperature such as about 35° or 45° to 65° C. In the high temperature aqueous treatment the fibers may be subjected to stretching, e.g. by about 50-75%. While for most uses the fibers need not have high strength properties, the alloy fibers have been found to retain to a large extent the physical properties of non-alloy rayon; for instance, using spinning and treatment conditions which gave a non-alloy control having a dry (conditioned) tenacity of about 2.9 g/d, dry elongation of about 20%, a dry modulus of about 72 g/d, a wet tenacity of about 1.6, a wet elongation of about 30%, and a wet modulus of 4.8 g/d, an alloy fiber (made from a spinning solution in which the ratio of cellulose to polyvinylpyrrolidone was about 69:31) showed a dry tenacity of about 2.4 g/d, a dry elongation of about 17%, a dry modulus of about 66 g/d, a wet tenacity of about 1 g/d, a wet elongation of about 27% and a wet modulus of about 4.1 g/d. With lower proportions of polyvinylpyrrolidone these physical properties are closer to those of the non-alloy fibers. Typically, the alloy fibers of this invention are not brittle and can be carded under conditions that cause fiber breakdown of more brittle (e.g. cross-linked) fibers. Also they swell to a greater degree in water than the non-alloy fibers.

The viscose which is employed in making the alloy fibers of the present invention is desirably of a composition as is used in making conventional regenerated cellulose fibers, e.g. a viscose produced by reacting alkali cellulose with carbon disulfide, with the resulting sodium cellulose xanthate being diluted with aqueous caustic to provide the resulting viscose with a desired cellulose and alkali content. For example, the viscose composition may contain cellulose ranging from 3 to about 12 wt. percent (e.g. 6 to 10%), caustic from about 3 to 12 wt. percent, and carbon disulfide, based on the weight of cellulose from about 20 to about 60%. Additives or modifiers may be mixed in the viscose if desired.

The polyvinylpyrrolidone preferably has a high molecular weight, such as well above 10,000. Very good results have been attained with polyvinylpyrrolidone of average molecular weight ranging from 100,000 to 400,000 and, more desirably, from 160,000 to 360,000, and a preferred K-value of from 50 to 100. The procecdure for determining the K-value of such polymers is known in the art, as disclosed in Modern Plastics, 1945, No. 3, starting on Page 157. Polyvinylpyrrolidone of desired character is commercially available, for example, under the designation of K-60 and K-90 from GAF corporation. Polyvinylpyrrolidone is described in Encyclopedia of Polymer Science and Technology, published in 1971 by John Wiley & Sons, in the article on "N-Vinyl Amide Polymers" in Volume 14, pages 239-251.

The polyvinylpyrrolidone may be the sole high polymeric additive in the viscose or it may be used together with other water-soluble (including aqueous alkali-soluble) high polymers. Preferably these are anionic polymers such as polymeric acids or salts (e.g. alkali metal salts) thereof, e.g. salts of carboxyalkyl celluloses (such as sodium carboxymethyl or carboxyethyl carboxyethyl cellulose), salts of polyacrylic acids, (including polyacrylic acid or polymethacrylic acid homo-polymer, or copolymers of acrylic and/or methacrylic acid with one or more other monomers such as acrylamide or alkyl acrylates, e.g. ethyl acrylate), salts of copolymers of maleic or itaconic acid with other monomers such as methyl vinyl ether, or naturally occurring polycarboxylic polymers, such as algin. These materials are preferably dissolved in aqueous medium before addition to the viscose, the solution being preferably alkaline, e.g., they may be made with an amount of alkali, such as NaOH, stoichiometrically equivalent to the amount of acidic (e.g. carboxyl) groups of the polymer or with an excess of alkali. Less desirably, these materials may be added in acid form (again preferably as aqueous solutions) and be converted to salt form by the action of the alkali present in the viscose. The anionic polymers may be those disclosed in the art as forming complexes with polyvinylpyrrolidone; see U.S. Pat. No. 2,901,457. Other water-soluble high polymers include substantially non-ionic polymers such as starch (which may be added as, say an alkaline solution containing some 2-5% of NaOH) or polyvinyl alcohol.

The proportion of polymer added to the viscose should be such as to impart improved fluid holding capacity to the rayon. Preferably it is such as to produce fibers whose fluid holding capacity (as measured by the "Syngyna" test described in Example III below) is at least 5 cc per gram and more, preferably at least 5.5 cc per gram. As will be seen below, the practice of this invention has made it possible to attain fluid holding capacities which are well above 6 cc per gram and even above 6.5 cc per gram. The fluid holding capacities attained in preferred forms of the invention are more than 20% better than those of fibers spun and processed under the same conditions but in the absence of the added polymer material; as can be seen from the Examples below this improvement is often greater than 25%, such as about 30, 40, 50, 60 or even 70%. In general the total proportion of added polyvinylpyrrolidone, alone or together with the anionic polymer, is within the range of about 6 to 40% based on the weight of cellulose in the viscose, and more desirably in the range of about 10 or 20 to 35%, based on the weight of cellulose. As shown below, higher proportions, e.g. about 50 or 70% may also be used. Expressed in terms of the toal of cellulose and added polymer (hereinafter termed "the total") the proportion of added polymer is generally in the range of about 7 to 30% such as about 10, 15 or 20%, although higher proportions may be employed. The proportion of polyvinylpyrrolidone, when used in combination with anionic polymer, is advantageously above 1% of the total, preferably above about 2 or 3% of the total such as about 5% or more of the total. In one preferred form the weight ratio of polyvinylpyrrolidone to anionic polymer is at least about 10:90, such as about 20:80, 30:70, 50:50, 70:30 or 80:20.

The polyvinylpyrrolidone described exhibits good solubility in water and aqueous solutions of polyvinylpyrrolidone, with or without added polymer, may be incorporated into the viscose at any stage, then blended and pumped to spinnerets for extrusion. After the spinning, coagulation, and regeneration stages, the shaped continuous tow of filaments undergoes the usual processing, which may include stretching if desired, and is then dried by conventional means. Generally, before drying, the continuous tow of filaments is cut into staple of a desired length. By the practice of the invention one can prepare alloy fibers of high fluid holding capacity which do not bond together during drying, even in the absence of applied finish, and can be subsequently carded with no difficulty by the manufacturer of articles incorporating such fibers. To aid in processing one may apply a lubricating finish, preferably of the hydrophilic type, e.g. a nonionic finish such as a Span or Tween (partial higher fatty acid, e.g. lauric, ester of sorbitan or mannitan or a polyoxyethylene derivative thereof) e.g. Span 20 or Tween 20. Such finish may be applied as a dilute aqueous dispersion thereof before drying. One may also treat the fibers with alkaline solutions to increase the pH of the dried fiber; treatments with alkaline solutions are described in some of the Examples and the alkali solution may be blended with the finish. The drying may be effected in any suitable manner, preferably by evaporating off the water by heat, e.g. in a hot air oven at moderate temperature (such as about 70° C) or a microwave oven. Typically drying is effected to such degree as to bring the moisture content of the fibers to about 8 to 20%, such as about 10–13%.

The alloy fibers of the present invention are adapted for use in a variety of articles, such as sanitary menstrual napkins and vaginal tampons, in which high fluid retention is an essential characteristic. In the manufacture of such articles, the alloy fibers necessitate no special techniques or equipment and they may be blended with other fibers which may or may not enhance the absorbent properties of the resulting articles. Fibers with which the alloy fibers of the present invention may be blended include, for example, rayon, cotton, chemically modified rayon or cotton, cellulose acetate, nylon, polyester, acrylic, polyolefin, etc. Typically a tampon is an elongated cylindrical mass of compressed fibers, supplied within a tube which serves as an applicator; see U.S. Pat. Nos. 2,024,218; 2,587,717; 3,005,456; 3,051,177.

The following Examples illustrate the invention further.

EXAMPLE I

Using conventional rayon spinning equipment, aqueous solutions of polyvinylpyrrolidone, designated as K-60 (GAF Corporation) and having an average molecular weight of about 160,000 and K-value of 50–62, were separately injected by a metering pump into a viscose stream during its passage through a blender and the blend thereafter extruded. During this the blend was subjected to high mechanical shearing. The viscose composition was 9.0% cellulose, 6.0% sodium hydroxide and 32% (based upon the weight of the cellulose) carbon disulfide. The viscose ball fall was 56 and its common salt test was 7.

The mixtures of viscose and polyvinylpyrrolidone were extruded through a 720 hole spinneret into a aqueous spinning bath consisting of 7.5% by weight of sulfuric acid, 18% by weight of sodium sulfate, and 3.5% by weight of zinc sulfate. After passage through the spinning bath, the resulting continuous tow was washed with water, desulfurized with an aqueous solution of sodium hydrosulifide, washed with water, acidified with an aqueous HCl solution, and again washed with water. The still wet multifilament tow was cut into staple fibers and, without any further treatment, dried.

The fluid-holding capacity of sample fibers, made with various approximate proportions (tabulated in Table I) of cellulose and polyvinylpyrrolidone in the spinning solution, was determined using the following test procedure.

Sample staple fibers were carried or otherwise well opened and then conditioned at 75° F and 58% relative humidity. Two grams of such alloy fibers were placed in a one-inch diameter die, pressed to a thickness of 0.127 inch, and maintained in this condition for one minute. This compressed pellet of fibers was removed from the die and placed on a porous plate of a Buchner funnel. The upper surface of the pellet was then engaged with a plunger which was mounted for free vertical movement, the plunger having a diameter of one inch and a weight of 2.4 pounds.

The funnel stem was connected by a flexible hose to a dropping bottle from which water was introduced into the funnel to wet the pellet of fibers. Control over the water flow was exercised by the position of the dropping bottle. After an immersion period of two minutes, the water was permitted to drain from the fiber pellet for three minutes, after which the still wet pellet was removed from the funnel and weighed. One-half of the weight of water in the sample pellet is a measure of the fluid-holding capacity of the fibers, expressed in cc/g.

The test results of sample fibers, as described above, are set forth in Table I.

EXAMPLE II

A 20% aqueous solution of polyvinylpyrrolidone, designated as K-90 (GAF Corporation) and having an average molecular lar weight of 360,000 and a K-value of 80–100, was injected into a viscose having a composition as described in Example I, after which the mixture was extruded as a continuous tow and processed as described above. The relative proportions of cellulose and polyvinylpyrrolidone in the spinning solution were 83:17. The resulting fibers had a fluid-holding capacity (tested as in Ex. I) which was 28% higher than conventional regenerated cellulose fibers.

EXAMPLE III

Aqueous solutions of polyvinylpyrrolidone, designated as K-90 (GAF Corporation) and having an average molecular weight of about 160,000 and K-value of 80–100, were separately injected into a viscose having a composition as described in Example I. In a manner as described in Example I, the mixtures of viscose and polyvinylpyrrolidone were shaped into a tow, treated with an aqueous solution containing 1.0% Span 20 and then cut into staple fibers.

Two and one-half grams of the different fibers prepared as described above were separately made into tampons by the following procedure: The fibers were carded into webs, each having a length of about 6 inches and being of variable thickness and width. Each of these webs was individually rolled in the direction of its width to provide a six inch roll and a string was looped about the center thereof. Each such roll was then folded on itself at the string loop and drawn into a ½ inch tube within which it was compressed by a clamp and plunger. After compression, the resulting tampons were removed, allowed to stand for a period of about 30 minutes during which the tampons recovered to a bulk density of about 0.4 cc/g and were then evaluated for their capacity to hold water by the Syngyna Method, as described by G. W. Rapp in a June 1958 publication of the Department of Research, Loyola University, Chicago, Ill. The results of such test are set forth in Table II for fibers made with various approximate proportions, as tabulated in Table II of cellulose and polyvinylpyrrolidone in the spinning solution.

EXAMPLE IV

A conventional, non-derivatized viscose, an aqueous solution of polyvinylpyrrolidone and a carboxyethyl cellulose (specifically a cyanoethylated viscose) were prepared separately. The composition of the non-derivatized viscose was 9.0% rayon cellulose, 6.0% sodium hydroxide and 32% carbon disulfide, based on the weight of the cellulose. This viscose had a ball fall of 56 seconds and its common salt test was 7.

The aqueous solution of polyvinylpyrrolidone was prepared simply by dissolving, in water, polyvinylpyrrolidone K-60.

Cyanoethylated viscose was prepared by premixing 8.25 lbs. of carbon disulfide and 10.75 lbs. acrylonitrile (34% and 45%, respectively, based on the weight of the cellulose), with the mixture then being charged into an evacuated churn by gravity through a valved stainless steel line. The churn contained a 77 lb. batch of alkali cellulose crumbs and was kept at a temperature of 15° to 32° C during a two hour reaction or churning period. Sufficient water and caustic were added to the churn after the two hour reaction period to provide a viscose of 8.0% cellulose and 6.0% sodium hydroxide (caustic) based on the weight of the viscose, and 34% carbon disulfide and 45% acrylonitrile based upon the weight of the cellulose, after mixing in the churn for an additional one and three quarter hours. The resulting cyanoethylated viscose had a common salt test of 17–21 and a ball fall of 40–50 seconds. Its content of cellulose derivative recoverable on spinning into, or precipitation by, a sulfuric acid spin bath was about 9%; this 9% value was used to calculate the proportions of such cellulose derivative (termed "CEC", for carboxyethyl-cellulose) in the Table III.

Using conventional spinning equipment, the alloying materials were injected into the non-derivatized viscose as hereafter set forth, with the resulting mixture being extruded through a 720 hole spinneret into an aqueous spinning bath consisting of 7.5% by weight of sulfuric acid, 18% by weight of sodium sulfate, and 3.5% by weight of zinc sulfate. After passage through the spinning bath, the resulting continuous tow was washed with water, desulfurized, acidified, and again washed with water in a manner as described in Example I. The still wet tow was cut into staple fibers which were treated with an aqueous solution containing 0.5% Span 20, dried, carded and then conditioned at 75° F and 58% relative humidity.

The fluid-holding capacity of sample unalloyed fibers and fibers containing the alloying components individually and in combination was determined using the test procedure described in Example I. The approximate proportions in the spinning solutions used for the unalloyed and alloyed fibers and the results of such tests are set forth in Table III.

It will be noted that conventional rayon fibers (Sample A), as produced from non-derivatized viscose, exhibit fluid-holding capacities which are less than those of alloy fibers produced from a mixture of conventional viscose and polyvinylpyrrolidone (Samples E and F) and that the fluid-holding capacities of fibers comprised of nonderivatized regenerated cellulose alloyed with regenerated cyanoethyl cellulose increase directly with the regenerated cyanoethyl cellulose content (Samples B, C and D). Significantly, notwithstanding the detrimental effects produced when the lower amounts of cyanoethylated viscose are employed alone as alloying agents, as illustrated by Samples B and C, such derivatized viscose, when combined with polyvinylpyrrolidone, does provide for a synergism, as exhibited by the remarkably improved fluid-holding capacities of the three-component alloy fibers indicated as Samples G and H.

The terminology "cyanoethylated viscose" as used herein refers to a viscose to which acrylonitrile is added or viscose prepared by the simultaneous cyanoethylation and xanthation of alkali cellulose. The latter procedure is preferred from the standpoint of economy and is described in U.S. Pat. Nos. 3,143,116 to A. I. Bates and 3,525,733 to I. K. Miller. Regeneration of such cyanoethylated viscose is accomplished by use of a conventional acidic type coagulating and regenerating bath, as described above. Hydrolysis of the cyanoethyl group on the cellulose during aging and processing produces predominately carboxyethyl substituent groups on the cellulose in place of the cyanoethyl groups in the resulting regenerated product. The term "regenerated cyanoethyl cellulose" as employed herein refers to a regenerated product as produced by the cyanoethylated viscose described.

Reference to the average degree of substitution (D.S.) of the cyanoethyl cellulose as used herein includes products wherein the anhydroglucose units of the cellulose molecules have an average substitution from about 0.25 to about 0.65 of cyanoethyl groups or chemical groups derived from said cyanoethyl groups by hydrolysis or other chemical change which occurs during manufacture and aging of the material. Thus, the recitation of cyanoethyl cellulose is also meant to include cellulose having carboxyethyl groups and some amidoethyl substituent groups.

EXAMPLE V

Example I was repeated, but instead of injecting the polyvinylpyrrolidone alone there was injected a blend of equal volumes of a 9% solution of the polyvinylpyrrolidone in water with a 9% solution of sodium carboxymethyl cellulose ("CMC") (Hercules grade 7 MF in 6% NaOH, D.S. of 0.7). Various amounts of this blend were used; specifically the proportions of cellulose; polyvinylpyrrolidone; and carboxymethyl cellulose were varied as follows: 100:00; 95:2 ½: 2 ½; 90:5:5; 85:7 ½: 7 ½; 80:10:10. A portion of the resulting fibers was finished with a ½% water solution of Span 20 (sorbitan monolaurate); and then dried; a second portion was made somewhat alkaline by washing in 1% aqueous solution of sodium bicarbonate, then rinsed in water before finishing with the ½% Span 20 solution and drying. The presence of the additive gave improved fluid-holding capacity (measured by the Syngyna test as in Example III); for instance, the 80:10:10 blend treated with sodium bicarbonate gave a fluid-holding capacity well above 6 cc/g.

EXAMPLE VI

Example I was repeated, but instead of injecting polyvinylpyrrolidone ("PVP") alone there was injected a blend of about 450 parts of a 6.7% aqueous solution of the polyvinylpyrrolidone K-90 and 550 parts of a 5.5% aqueous alkaline solution of polyacrylic acid ("PAA"). The latter was made by diluting 120 grams of Rohm & Haas "Acrysol A-5" (a 25% aqueous solution of a polyacrylic acid) with 338 ml of water, then adding a stoichiometric amount of alkali, namely 92 grams of 18% aqueous NaOH solution. The K-90 solution was then added to the polyacrylate solution with stirring and the resulting blend was a clear solution containing about 3% of each of the polymers. Various amounts of the blend were used; specifically the proportions of cellulose; polyvinylpyrrolidone; polyacrylic acid; were varied as follows: 100:00; 95:2 ½; 90:5:5; 85:7 ½: 7 ½; 80:10:10. A portion of the resulting fibers was finished with a ½% water solution of Span 20 and then dried. A second portion was made somewhat alkaline by washing in a 1% aqueous solution of sodium bicarbonate, then rinsed in water before finishing with the ½% Span 20 solution and drying. The presence of the additives gave improved fluid-holding capacity (measured by the Syngyna test as in Example III); for instance, the 90:5:5; 85:7 ½: 7 ½; and 80:10:10 blends each gave a fluid-holding capacity well above 6 cc/g.

When the polyacrylic acid was only partially neutralized (e.g. neutralized with only 70% of the stoichiometric proportion of NaOH) before blending with the polyvinylpyrrolidone the improvement was not as marked. Thus with 85 parts cellulose, 7 ½ parts PVP, 7 ½ parts PAA (or 10 PVP and 5 PAA; or 5 PVP and 10 PAA) the fluid-holding capacity was about 20-25% better than the control (100 cellulose) when such partially neutralized PAA was used. It is therefore preferred that the amount of alkali present in the system be at least equal to or greater (e.g. 20-30% greater) than the amount necessary to neutralize all the acidic groups of the added anionic polymer.

EXAMPLE VII

Example I was repeated except that the solution injected was prepared as follows: A carboxyethyl starch ("CES") solution containing 9% starch was prepared (see Ex. 1 of U.S. 3,847,636) with enough acrylonitrile added to give a degree of substitution of 0.7. To a volume of this solution was added an equal volume of 9% aqueous solution of PVP K-60. The resulting blend of polymer solutions (as tabulated in Table IV) was used for injection into viscose and subsequent spinning of fibers. The fibers were processed as described in Example I. To one portion a ½% Span 20 finish solution applied and then the fibers were dried. A second portion was immersed in 1% aqueous NaHCO$_3$, then in ½% Span 20 and dried.

The evaluation for fluid-holding by the Syngyna test gave results as set forth in Table IV.

EXAMPLE VIII

Example I was repeated with the following changes: The solutions for injection into the viscose were prepared as follows. A carboxymethyl starch (CES) solution was prepared as stated in Example VII. One solution for injection comprised equal parts of the above CES solution with 9% aqueous PVP K-90. A second solution for injection comprised three parts of the above CES solution with one part of a 9% aqueous solution of PVP K-90. Fibers were then spun by blending with viscose (as tabulated in Table V). The fibers were processed as described in Example I and finished in an aqueous solution of ½% Na$_2$HPO$_4$ and the results being given in Table V.

EXAMPLE IX

Using conventional rayon spinning equipment alloy rayon fibers were produced containing vinylmethylether-maleic copolymer and polyvinylpyrrolidone K-90. Various blends, in proportations tabulated in Table VI below, were made of
(1) a 10% solution of the PVP K-90 (GAF Corporation), in water and
(2) a solution made by dissolving 100 parts of Gantrez AN-149 GAF Corporation (vinylmethylether-maleic anhydride copolymer) in a mixture of 285 parts of 18% aqueous solution of NaOH and 626 parts of water (thus hydrolyzing and neutralizing anhydride groups of the copolymer).

The resulting blends were injected, as in Example I, into the viscose which was then extruded through a 980 hole spinneret into an aqueous spinning bath at 55° C containing 7.2% H$_2$SO$_4$, 22% Na$_2$SO$_4$ and .6% ZnSO$_4$. The resulting tow was then stretched about 75% while passing through an aqueous bath containing 2 ½% H$_2$SO$_4$ at about 90° C, and formed into skeins. The skeins were washed in water at about 60° C and cut to form staple fibers. One portion of the washed fibers (Samples A, B and C) was finished with 0.1% aqueous solution of Span 20 and dried at about 70° C. A second portion of the washed fibers (Samples D, E and F) was treated with a half percent aqueous solution of NaOH, then washed with softened water (which was slightly alkaline) then finished with a 0.2% aqueous solution of Tween 20 and dried at about 70° C. The tabulation in Table VI gives the proportions of the added ingredients, the results obtained in Syngyna Tests, and the pH values for 1% slurries of the fibers in distilled water.

The more preferred fibers of this invention show a pH (measured in a mixture of 100 parts distilled water and one part of fibers) of well above 6 and generally at least about 7, such as about 8, 9 or 9.5.

It is within the broader scope of this invention to employ in place of all or part (e.g. ⅓, ½ or ⅔), of the polyvinylpyrrolidone, one or more other N-vinyl amide polymers, e.g. N-vinyl lactam polymers, N-vinyl-2 of azolidinone polymers or N-vinyl-3-morpholinone polymers such as the polymers (including copolymers) listed in U.S. Pat. No. 2,931,694, issued Apr. 5, 1960.

It will be noted that in the foregoing Examples, the fibers, as spun, are unpigmented and undyed. It is of course within the broader scope of the invention, although not at all necessary for practicing it, to incorporate pigment or dye into the spinning solution.

Fibers described in the above Examples had a denier per filament of about 3. It will be understood, of course, that the spinning may be effected to produce other deniers such as 1.5, 4, 5.5 and 8 denier per filament.

TABLE I

| Sample | Cellulose | Polyvinyl-pyrrolidone | Fluid-Holding Capacity cc/g | % Water Retention |
|---|---|---|---|---|
| A | 100 | 0 | 3.06 | 105 |
| B | 95 | 5 | 3.16 | 112 |
| C | 90 | 10 | 3.52 | 121 |
| D | 80 | 20 | 4.15 | 145 |
| E | 70 | 30 | 4.69 | 186 |
| F | 65 | 35 | 4.68 | 178 |
| G | 60 | 40 | 4.65 | 190 |

% Water Retention is the percent water retained by the loose mass of fibers after centrifuging the same at 1 G for 3.5 minutes.

TABLE II

| Sample | Cellulose | Polyvinyl-Pyrrolidone | Fluid-Holding Capacity cc/g |
|---|---|---|---|
| J | 100 | 0 | 4.36 |
| K | 90 | 10 | 4.84 |
| L | 85 | 15 | 5.38 |
| M | 80 | 20 | 5.46 |
| N | 75 | 25 | 5.65 |

TABLE III

| Sample | Cellulose | CEC | Polyvinyl-pyrrolidone | Fluid-Holding Capacities cc/g. |
|---|---|---|---|---|
| A | 100 | 0 | 0 | 3.06; 3.07; 3.14; 3.16 |
| B | 90 | 10 | 0 | 2.50; 2.55 |
| C | 80 | 20 | 0 | 2.95; 3.3 |
| D | 60 | 40 | 0 | 3.35; 3.5 |
| E | 90 | 0 | 10 | 3.52; 3.53 |
| F | 70 | 0 | 30 | 4.68; 4.70 |
| G | 75 | 12.5 | 12.5 | 5.03; 5.04 |
| H | 65 | 17.5 | 17.5 | 5.37; 5.39 |

TABLE IV

| Sample | Cellulose | CES (Expressed in Terms of Starch Content) | PVP | Fluid Holding Capacity cc/g | |
|---|---|---|---|---|---|
| | | | | Without NaHCO$_3$ Treatment | With NaHCO$_3$ Treatment |
| A | 100 | 0 | 0 | 4.3 | 4.0 |
| B | 90 | 5 | 5 | 4.8 | 4.2 |
| C | 80 | 10 | 10 | 4.7 | 5.2 |
| D | 70 | 15 | 15 | 4.9 | 5.2 |

TABLE V

| Sample | Cellulose | CES (Expressed in Terms of Starch Content) | PVP | Fluid Holding Capacity cc/g |
|---|---|---|---|---|
| A | 100 | 0 | 0 | 4.08 |
| B | 89.2 | 5.4 | 5.4 | 4.80 |
| C | 80 | 10 | 10 | 5.44 |
| D | 80 | 15 | 5 | 5.40 |
| E | 89.2 | 8.1 | 2.7 | 4.80 |

TABLE VI

| Sample | Cellulose | PVP | Gantrez AN-149 | pH | Fluid Holding Capacity cc/g |
|---|---|---|---|---|---|
| A | 85.2 | 9.9 | 4.9 | 6.8 | 5.0 |
| B | 85.2 | 7.4 | 7.4 | 7.4 | 5.3 |
| C | 85.2 | 4.9 | 9.9 | 8.3 | 5.9 |
| D | 85.2 | 9.9 | 4.9 | 8.8 | 5.75 |
| E | 85.2 | 7.4 | 7.4 | 9.1 | 5.78 |
| F | 85.2 | 4.9 | 9.9 | 9.2 | 5.89 |

I claim:

1. Alloy rayon fibers of higher fluid-holding capacity than non-alloy rayon, comprising a regenerated cellulose matrix and a water soluble polymer dispersed therein in an amount sufficient to increase the fluid-holding capacity by more than 20% and to attain a fluid-holding capacity in the Syngyna test of at least five cc per gram, said water soluble polymer comprising an N-vinylamide polymer which is a polymer of one or more of the monomers vinylpyrrolidone, N-vinyl lactam, a N-vinyl-2-oxazolidinone or a N-vinyl-3-morpholinone.

2. Fibers as in claim 1 containing a polymer of vinylpyrrolidone.

3. Fibers as in claim 1 in which a water soluble anionic polycarboxylic polymer is also dispersed in said matrix, said polymer being selected from the group consisting of salts of carboxyalkyl cellulose, salts of polyacrylic acids, salts of copolymers of acrylic acid and copolymers of methacrylic acid with one or more other monomers, salts of copolymers of maleic or itaconic acid with vinyl methyl ether and naturally occurring algins.

4. Fibers as in claim 3 containing polyvinylpyrrolidone and carboxymethyl cellulose dispersed therein.

5. Fibers as in claim 3 containing polyvinylpyrrolidone and a salt of a polyacrylic acid dispersed therein.

6. Fibers as in claim 3 containing polyvinylpyrrolidone and a salt of a maleic anhydride-vinylmethyl ether copolymer dispersed therein.

7. Fibers as in claim 3 in which the weight ratio of said N-vinylamide polymer to said anionic polycarboxylic polymer to at least about 10:90.

8. Fibers as in claim 7 in which the weight ratio of said amide polymer to said polycarboxylic polymer ranges from about 20:80 up to about 80:20.

9. Process for making alloy rayon fibers, of higher fluid-holding capacity than non-alloy rayon, comprising a regenerated cellulose matrix and a water soluble polymer dispersed therein in an amount sufficient to increase the fluid-holding capacity by more than 20% and to attain a fluid holding capacity in the Syngyna test of at least five cc per gram, said water soluble polymer comprising an N-vinylamide polymer which is a polymer of one or more of the monomers vinylpyrrolidone, N-vinyl lactam, a N-vinyl-2-oxazolidinone or a N-vinyl-3-morpholinone which comprises spinning into a coagulating bath a blend of viscose and said water-soluble polymer to form fibers, the proportions of said dispersed polymer being at least about 7% of the total.

10. Process as in claim 9 in which proportion of the said polymer is at least 10% of the total.

11. Fibers made by the process of claim 10.

12. Process for making alloy rayon fibers of higher fluid-holding capacity than non-alloy rayon, comprising a regenerated cellulose matrix and a water soluble polymer dispersed therein in an amount sufficient to increase the fluid-holding capacity by more than 20% and to attain a fluid holding capacity in the Syngyna test of at least five cc per gram, said water soluble polymer comprising an N-vinylamide polymer which is a polymer of one or more of the monomers vinylpyrrolidone, N-vinyl lactam, a N-vinyl-2-oxazolidinone or a N-vinyl-3-morpholinone and a water soluble anionic polycarboxylic polymer selected from the group consisting of salts of carboxyalkyl cellulose, salts of copolymers of acrylic acid and copolymers of methacrylic with one or more other monomers, salts of copolymers of maleic or itaconic acid with vinyl methyl ether and naturally occurring algins which comprises spinning into a coagulating bath a blend of viscose, said N-vinyl amide polymer and said anionic polycarboxylic polymer, to form fibers, the proportions of said polymer being at least about 7% of the total.

13. Process as in claim 12 in which said N-vinyl amide polymer comprises polyvinylpyrrolidone.

14. Process as in claim 13 in which the anionic polymer comprises carboxymethyl cellulose.

15. Process as in claim 13 in which the anionic polymer comprises a salt of a polyacrylic acid.

16. Process as in claim 13 in which the anionic polymer comprise vinyl methyl ether-maleic acid copolymer.

17. Fibers made by the process of claim 13.

18. A vaginal tampon comprising a mass of fibers of claim 1.

19. A vaginal tampon comprising a mass of fibers made by the process of claim 13.

* * * * *

UNITED STATES PATENT AND TRADEMARK OFFICE
CERTIFICATE OF CORRECTION

PATENT NO. : 4,136,697

DATED : January 30, 1979

INVENTOR(S) : Frederick R. Smith

It is certified that error appears in the above—identified patent and that said Letters Patent are hereby corrected as shown below:

Col. 2, line 45: entire line should read "as sodium carboxymethyl or carboxyethyl".
Col. 4, line 40: "hydrosulifide" should read "hydrosulfide".
Col. 4, Line 49: "carried" should read "carded".
Col. 5, line 9: "molecular lar" should read "molecular".
Col. 5, line 42: "0.4% cc/g" should read "0.4 g/cc".
Col. 7, line 26: "100:00" should read "100:0:0".
Col. 7, line 55: "100:00" should read "100:0:0".
Col. 7, line 55: "95:2½" should read "95:2½:2½".
Col. 8, line 33: "carboxymethyl" should read "carboxyethyl".

Signed and Sealed this

Twenty-third Day of October 1979

[SEAL]

Attest:

RUTH C. MASON
Attesting Officer

LUTRELLE F. PARKER
Acting Commissioner of Patents and Trademarks